United States Patent
Slavicek

(10) Patent No.: US 7,946,847 B2
(45) Date of Patent: May 24, 2011

(54) INCISAL GUIDING TABLE FOR DENTAL ARTICULATORS OR THE LIKE

(75) Inventor: Rudolf Slavicek, Vienna (AT)

(73) Assignee: Gamma Medizinisch Wissenschaftliche Fortbildungs-Ges.m.b.H., Klosterneuburg (AT)

( * ) Notice: Subject to any disclaimer, the term of this patent is extended or adjusted under 35 U.S.C. 154(b) by 496 days.

(21) Appl. No.: 10/491,581

(22) PCT Filed: Aug. 2, 2002

(86) PCT No.: PCT/AT02/00233
§ 371 (c)(1),
(2), (4) Date: Apr. 1, 2004

(87) PCT Pub. No.: WO2004/012623
PCT Pub. Date: Feb. 12, 2004

(65) Prior Publication Data
US 2004/0241607 A1    Dec. 2, 2004

(51) Int. Cl.
*A61C 11/00* (2006.01)
(52) U.S. Cl. .......................................................... 433/59
(58) Field of Classification Search .............. 433/53–67, 433/229
See application file for complete search history.

(56) References Cited

U.S. PATENT DOCUMENTS

| | | | | |
|---|---|---|---|---|
| 2,608,761 A | | 9/1952 | Scott | 32/32 |
| 3,769,708 A | | 11/1973 | Guichet | 32/32 |
| 4,035,916 A | * | 7/1977 | Eveland | 433/58 |
| 4,505,674 A | | 3/1985 | Edwardson | 433/59 |
| 5,020,993 A | * | 6/1991 | Levandoski | 433/65 |
| 5,366,373 A | | 11/1994 | Mumolo et al. | 433/58 |
| 5,707,233 A | | 1/1998 | Hobo et al. | 433/55 |
| 6,386,868 B1 | * | 5/2002 | Fujita | 433/60 |

FOREIGN PATENT DOCUMENTS
DE    295 12 681    11/1995

* cited by examiner

*Primary Examiner* — Cris L Rodriguez
*Assistant Examiner* — Hao D Mai
(74) *Attorney, Agent, or Firm* — Cohen Pontani Lieberman & Pavane LLP

(57) ABSTRACT

An incisal guide for dental articulators or the like provided with an upper and a lower component which are movable relative to each other by way of a joint, the incisal guide being mountable on the upper or lower component and provided with a guide surface inclined with respect to a reference plane upon which an incisal pin is bearing and which, with a line of application of the greatest bearing force component denominated as normal, encloses an angle corresponding to the angle of protrusion and laterotrusion alignment of the human denture, at least one incisal table guide surface inclined relative to a reference plane being provided which may be positioned by a guide surface adjustment device, the articulator incisal pin during movement simulation moving over the predetermined incisal guide way on the incisal guide surface.

6 Claims, 6 Drawing Sheets

US 7,946,847 B2

INCISAL GUIDING TABLE FOR DENTAL ARTICULATORS OR THE LIKE

RELATED APPLICATIONS

This is a U.S. National Phase Application under 35 U.S.C. 371 of International Application PCT/AT02/00233 filed on Aug. 2, 2002.

BACKGROUND OF THE INVENTION

1. Field of the Invention

The invention relates to an incisal guide for dental articulators or the like provided with an upper and a lower component which are movable relative to each other by way of a joint, the incisal guide being mountable on the upper or lower component and provided with a guide surface inclined with respect to a reference plane upon which an incisal pin is supported and which, with a line of application of the greatest support force component denominated as normal, encloses an angle corresponding to the angle of protrusion and laterotrusion alignment of the human denture, the incisal pin, during simulated movement, moving across the predetermined incisal guide surface which may be selected and positioned by one or a combination of rotating, tilting, pivoting or shifting a guide surface block.

The dental articulator in essence corresponds to a motion simulator for representing mandible movements, these movements consisting of a translational as well as a rotational component of the axis of the joint of the jaws. In general, articulators are configured to consist of an upper and a lower component. As a rule, the impression model of the superior dental arch is mounted on the upper component and the impression model of the inferior dental arch is mounted on the lower component. In this connection, the models are mounted in a spatial alignment relative to a reference plane and to the jaw joint axis according to the conditions of an individual patient. The articulator is usually provided with two rear joint boxes which simulate the human jaw joint. By known methods the joint boxes are adjusted in all dimensions according to individual patients or according to statistical mean values. The posterior guides are predetermined in accordance with individual patients or statistical mean values and define the movements of the jaw joints in a translational direction of movement.

As regards the reconstruction of dental occlusal surfaces, the movement of the teeth relative to each other is decisive. During a laterotrusional movement, the crown of a lateral lower jaw tooth usually slides along a guide surface of the complementary opposite tooth on the upper jaw. The type of guide surfaces of all existing lateral teeth and their interaction during the course of their movement result in a so-called occlusion concept which in a natural set of teeth is usually shown as all teeth guiding during the initial laterotrusion movement, but that during continued excursion movement of the jaw joint the guides of the front teeth sequentially disocclude the rear teeth, i.e. the crown of the lower jaw tooth is lifted off the guide surface of the upper jaw tooth.

When fabricating prosthetic occlusion surfaces of teeth attempts are thus made to copy this occlusion guide concept in order to attain as high as possible a chewing efficiency in the prosthetic reconstruction. However, for reasons of dental medicine, dental technology or material technology, aside from the above mentioned natural sequential guide, other existing guide concepts (group function, canine guide, etc.) may be indicated.

2. The Prior Art

An incisal guide table is necessary for effectively putting such a concept of reconstruction into practice. Such tables as known, for instance, from German patent specifications DE 29 512 680 and DE 29 512 681 U1 are provided with a guide surface inclined relative to a reference plane. During movement, the incisal pin slides upon the guide surface. The forward slide surface forces the articulator into an additional rotational movement. This in common with the posterior controls of the two joint boxes results in the overall definition of the spatial lower jaw movement. It is thus possible, on the teeth of the upper jaw effectively to fabricate the steepness and disposition of the guide surface.

The guide surfaces of known incisal table systems are usually either permanently preset or they may be pivoted to, and arrested at, certain angles. Permanently preset Incisal table systems suffer from the drawback that during movement simulation they generate a guide system in which all teeth of one side guide simultaneously during laterotrusional movement. Often, such a guide concept is undesirable.

The complicated operation of adjustable incisal table systems has been found to be a disadvantage because for attaining guide surfaces, depending upon the concept, a different value, derived in advance by complex calculation with a computer program and displayed in a table, must be set for each tooth. Moreover, the use of such a system places high demands upon a dental technician. Often, the economic application and the putting into practice of a occlusion concept fails as a result of the complexity of the application and because the additional great complexity is not being paid for.

OBJECT OF THE INVENTION

It is an object of the invention to provide an incisal guide table of the kind referred to initially which makes it possible in a simple manner to put into practice predetermined occlusion concepts by avoiding complicated calculation and adjustment processes and to simulate laterotrusion, protrusion, retrusion and transitional movements.

BRIEF SUMMARY OF THE INVENTION

In accordance with the invention the object is accomplished by the guide surfaces of the guide block resulting in the form of a spiral stair or screw surface, the pitch of the spiral or screw surface being either constant or not constant, or by the guide surfaces being surfaces generated by numerical processes.

In this manner it is possible to achieve simple manipulation in practicing predetermined occlusion concepts by avoiding complicated calculation and adjustment processes.

In accordance with a preferred embodiment of the invention the guide way on the guide surface may be selected by positioning the tip of the incisal pin by one or a combination of rotating, tilting, pivoting or shifting. The guide surface block may be adjustable continuously and/or by a rigid raster and may be arrested by clamping and/or latching, the position being preferably indicated by a dial. Advantageously the guide surface block may be adjusted by semi or fully automatic controls.

In accordance with another embodiment of the invention the protrusive and/or retrusive and/or right latero-protrusive and/or left latero-protrusive guide surfaces of the guide surface block are of unitary structure.

In the context of the invention the protrusive and/or retrusive and/or right latero-protrusive and/or left latero-protrusive guide surface of the guide surface block is exchangeable. Preferably, exchangeable guide surface segments are provided.

DESCRIPTION OF THE SEVERAL DRAWINGS

The novel features which are considered to be characteristic of the invention are set forth with particularity in the appended claims. The invention itself, however, in respect of its structure, construction and lay-out as well as manufacturing techniques, together with other objects and advantages thereof, will be best understood from the following description of preferred embodiments when read in connection with the appended drawings, in which:

FIG. 1 is a schematic presentation of a part of an incisal guide table in accordance with the prior art;

FIGS. 2a, b; 3a, b and 4a, b each schematically depict embodiments of the incisal guide table in accordance with the invention in a partial sectional view;

DETAILED DESCRIPTION OF THE PREFERRED EMBODIMENTS

The incisal guide table shown is used for dental articulators and the like which are provided with an upper and a lower component and which may be moved relative to each other by means of a joint. The incisal guide table may be mounted on the upper or lower component of the articulator.

Figure 1:
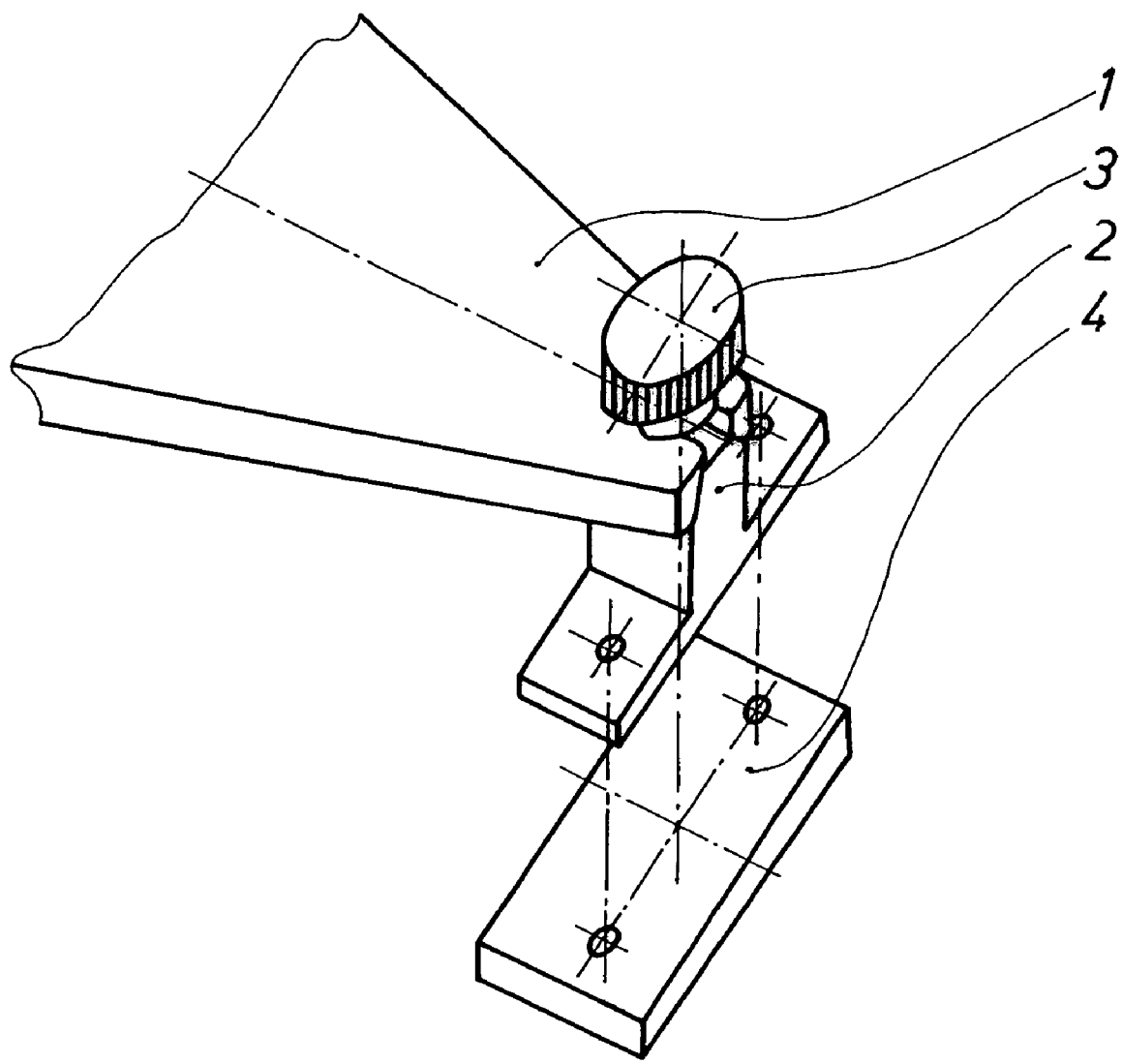

FIG. 1 depicts an upper component 1 of an articulator in accordance with the prior art provided with a support 2, affixed to the upper component of the articulator by rotatable knob 3 with a screw extending therefrom. The guide surface adjustment device 4 is mounted on the support 2.

Figure 2A:
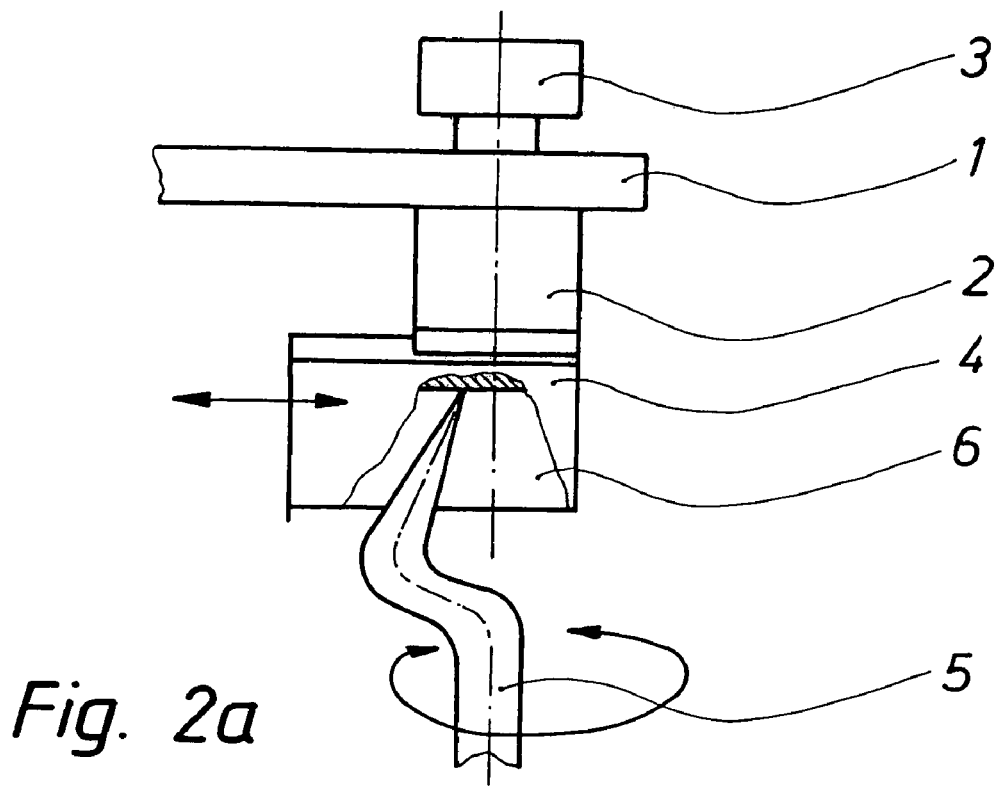
Figure 2B:
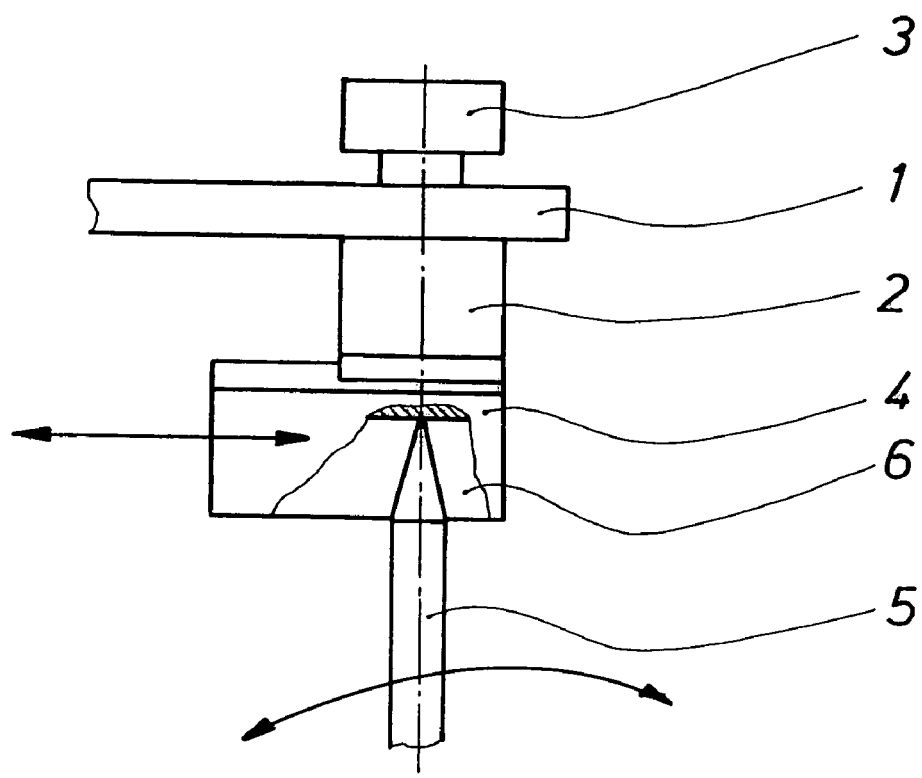

As shown in FIG. 2a an adjustment device 4 in accordance with the invention is provided with an eccentrically bent incisal pin 5. By rotating the incisal pin 5 along its lower longitudinal axis or, as shown in FIG. 2b, by pivoting or shifting of the incisal pin 5, the setting may be changed. Hence, by rotation and/or tilting and/or pivoting and/or shifting of the incisal pin the tip of the incisal pin 4 may be position such that a desired guide way may be selected on the guide surface 6 of the incisal table.

Figure 3A:
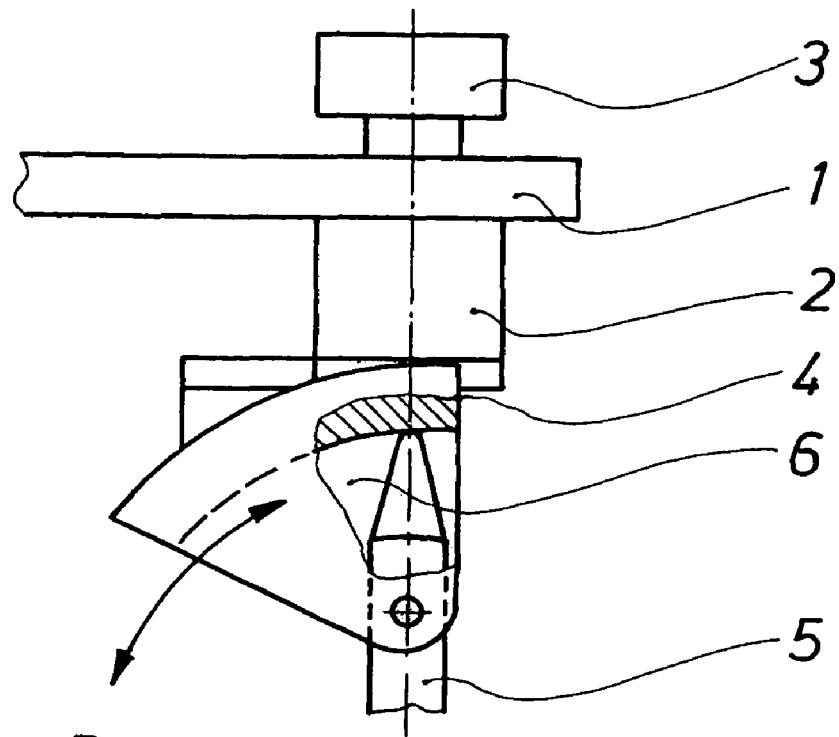
Figure 3B:
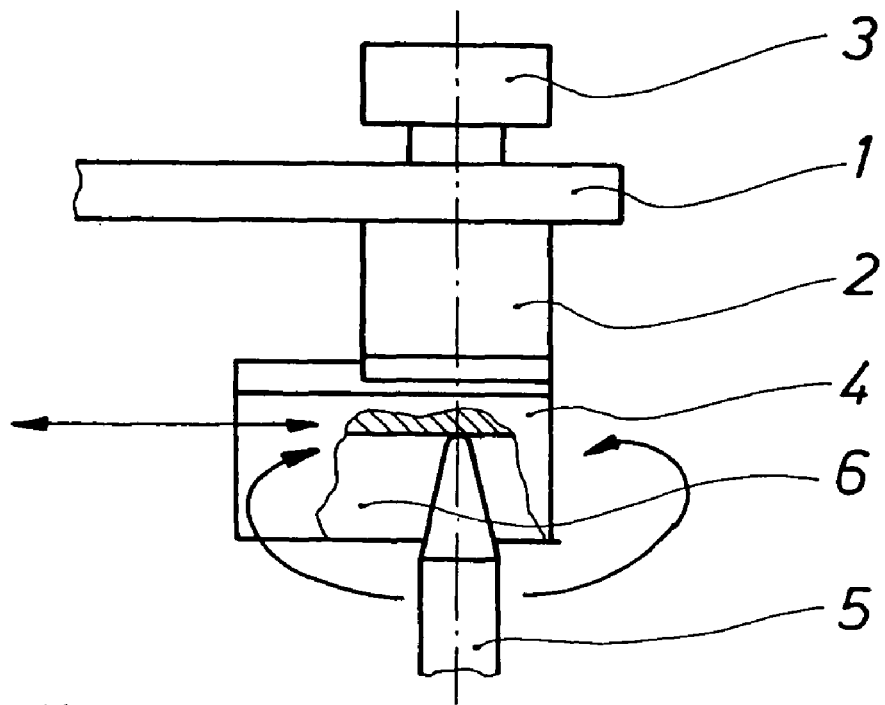

As shown in FIG. 3a a pivotal guide surface adjustment device 4 is provided in another embodiment in which the imaginary fulcrum is positioned below. FIG. 3b depicts a horizontally shiftable and/or rotatable guide surface adjustment device 4.

Figure 4A:
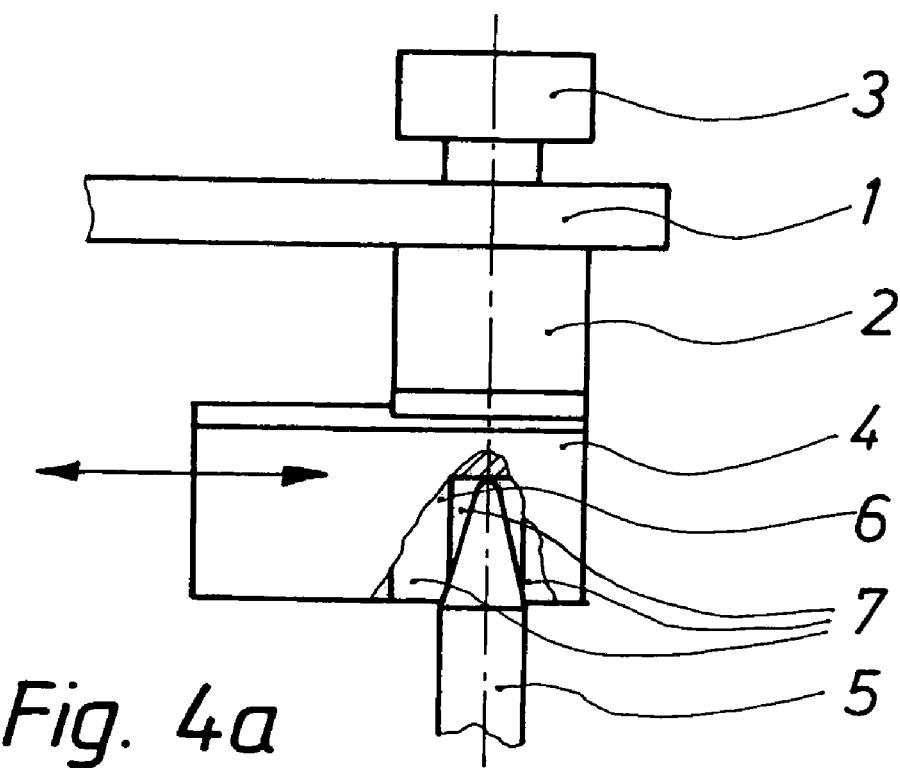
Figure 4B:
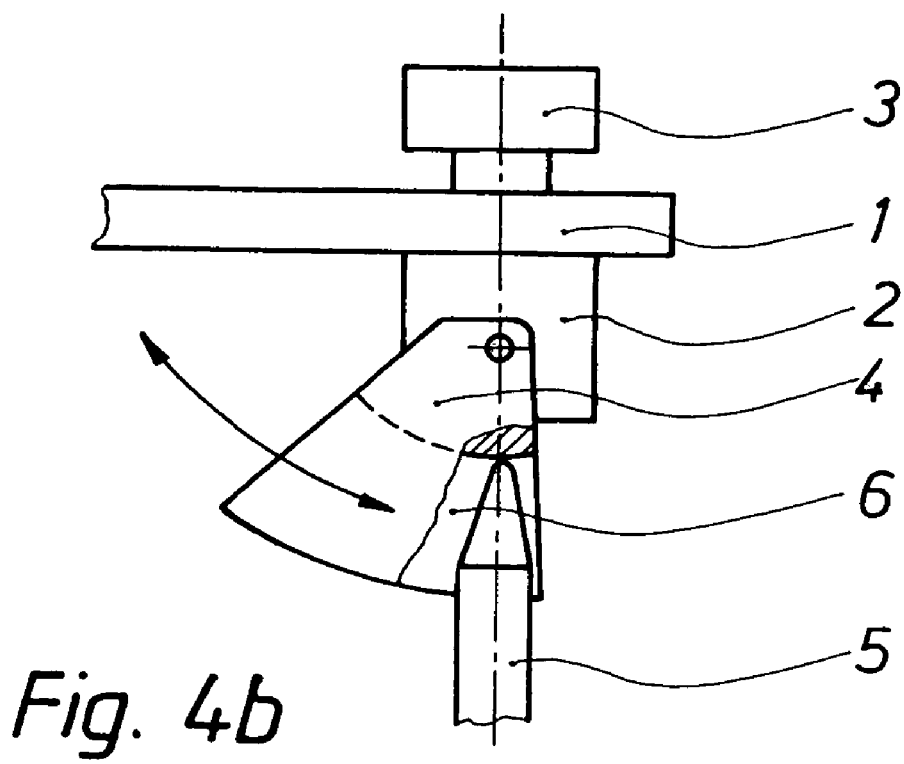
Figure 5A:
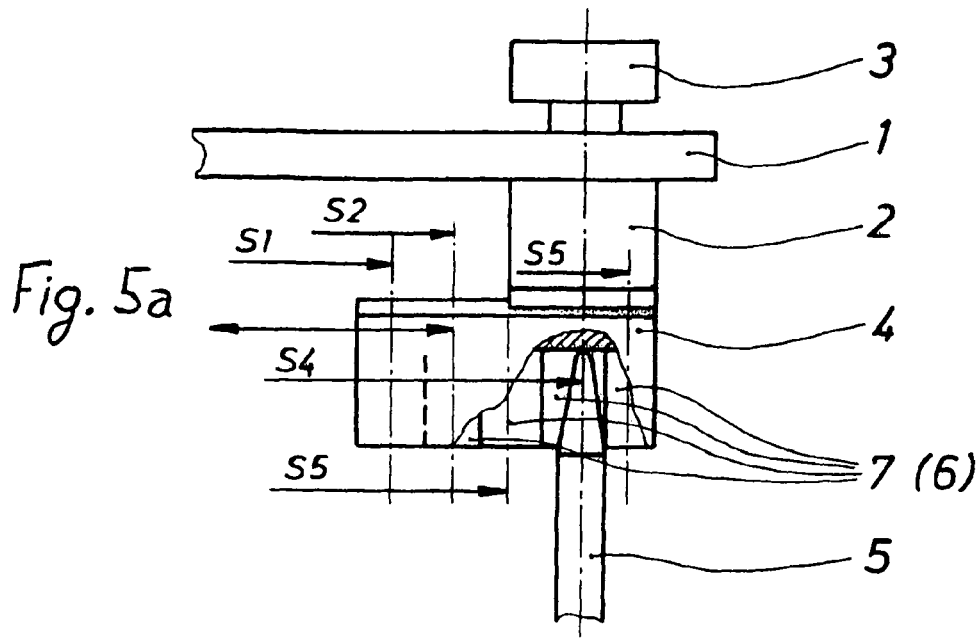
FIG. 5a is an elevational view of a dental articulator in accordance with an embodiment of the invention.
Figure 5:
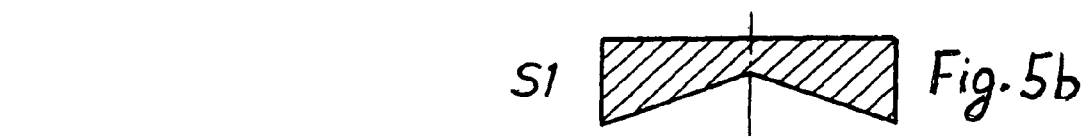
FIGS. 5b, 5c, 5d, 5e and 5f are respective views of sections S1, S2, S3, S4 and S5 of the guide surface block as depicted in FIG. 5a, and FIGS. 6 and 7 depict two models.
Figure 5:
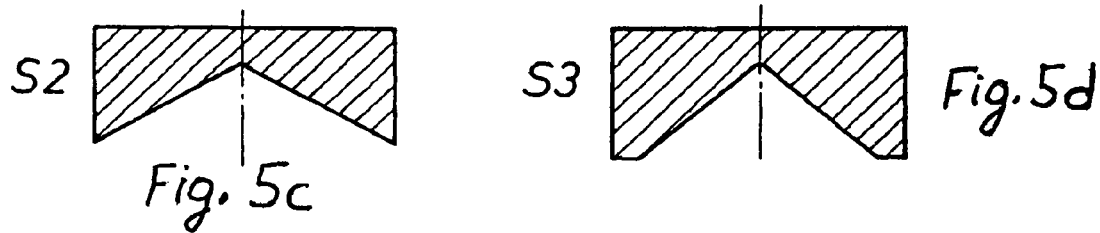
Figure 5:
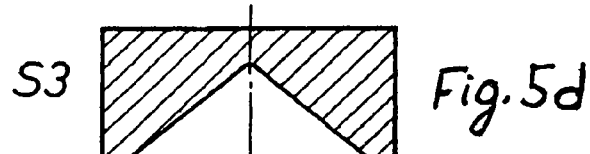
Figure 5:
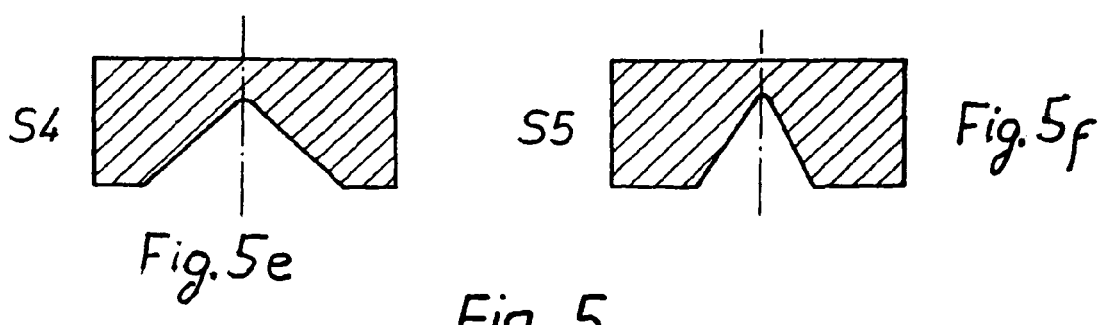
Figure 5:
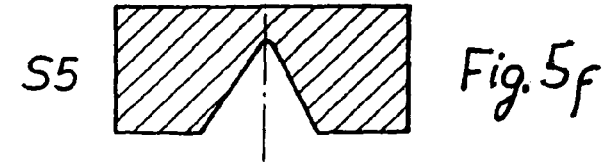

FIG. 4a depicts a different embodiment with a horizontally shiftable and/or rotatable guide surface adjustment device 4 in which the guide surfaces 6 are constituted by a plurality of surfaces in an arrangement resembling a spiral stair. FIG. 4b depicts a pivotal guide surface adjustment device 4 with an imaginary fulcrum disposed above.

It is thus possible to select any given incisal guide surface by rotating and/or tilting and/or pivoting and/or shifting of the guide surface block 4. In accordance with the invention the guide surface adjustment device 4 may be structured such that the adjustment occurs continuously or in accordance with rigid steps and it may be arrested by clamping and/or latching. The position may be indicated by a dial.

Figure 6:
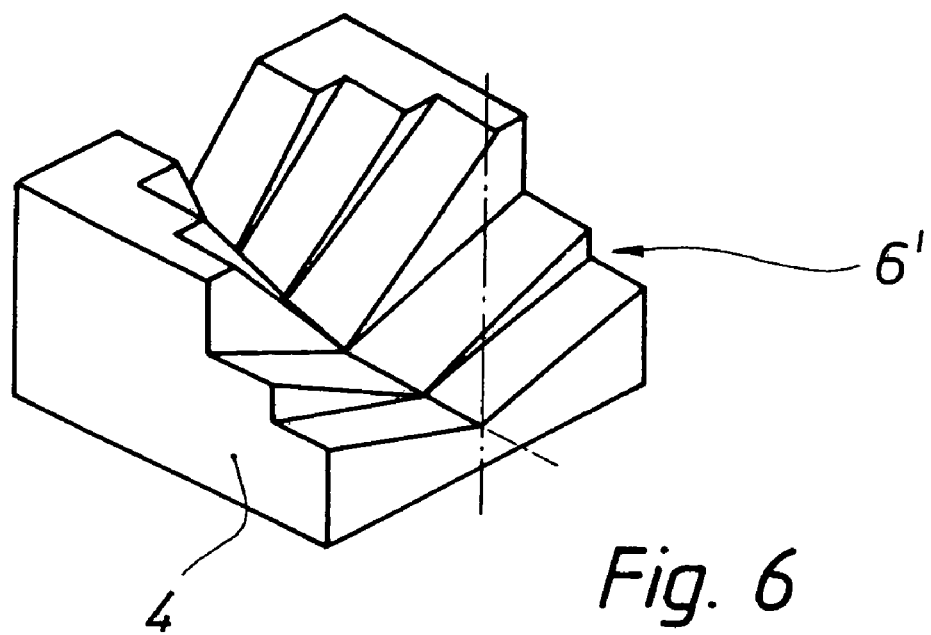
Figure 7:
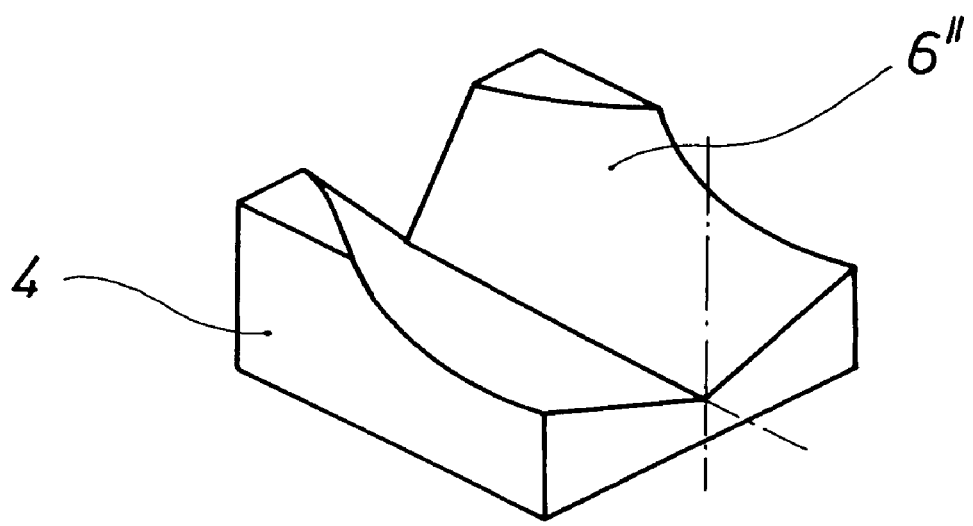

FIGS. 6 and 7 depict a guide surface block 4 with a spiral stair or screw-like structure of the surface.

In an embodiment not shown, the positional adjustment may be provided by semi or fully automatic controls.

What is claimed is:

1. A dental articulator, comprising:
   an upper component;
   a lower component;
   an incisal pin coupled to one of said upper and lower components;
   a joint movably coupling said upper and lower components to each other to effect movement simulation representing mandible movements;
   an incisal guide table mounted on the other of said upper and lower components, and having a plurality of inclined guide surfaces inclined as progressive steps relative to a reference plane and arranged into a plurality of progressive pairs of inclined guide surfaces, wherein each of said plurality of progressive pairs of inclined guide surfaces forms a V-shape having a common root with other progressive pairs of said plurality of inclined guide surfaces, said incisal guide table and said incisal pin being adjustably positioned relative to each other such that said incisal pin engages a selected portion of one of said plurality of inclined guide surfaces and moves thereacross during the movement simulation;
   wherein said selected portion of one of said plurality of inclined guide surfaces engaged by said incisal pin applies a supporting force to said incisal pin and which together with a line of application of greatest force component of the supporting force includes an angle corresponding to an angle of the protrusion and laterotrusion guide of a human denture.

2. The dental articulator of claim 1, wherein a pitch of said plurality of inclined guide surfaces is constant.

3. The dental articulator of claim 1, wherein a pitch of said plurality of inclined surfaces is not constant.

4. The dental articulator of claim 1, wherein a pitch of said plurality of inclined guide surfaces is generated numerically.

5. The dental articulator of claim 1, further comprising securing means for securing said incisal guide table to the other of said upper and lower components to be selectively adjustable relative thereto into any of a plurality of positions and/or angles.

6. The dental articulator of claim 1, wherein said incisal pin is eccentrically bent so that its tip is shifted out of said incisal pin's longitudinal axis.

* * * * *